United States Patent [19]

Markezich et al.

[11] 4,128,574

[45] Dec. 5, 1978

[54] METHOD FOR MAKING ORGANIC POLYCARBOXYLIC ACIDS

[75] Inventors: Ronald L. Markezich; Tohru Takekoshi, both of Scotia, N.Y.

[73] Assignee: General Electric Company, Schenectady, N.Y.

[21] Appl. No.: 729,126

[22] Filed: Oct. 4, 1976

[51] Int. Cl.$^2$ ............................................. C07C 65/14
[52] U.S. Cl. ................................ 562/473; 260/307 H; 260/326 R; 260/326 A; 260/326.26; 562/474; 562/432; 562/429; 562/460; 562/463; 562/469
[58] Field of Search ........... 260/520 E, 326 R, 326 A, 260/326.26

[56] References Cited

U.S. PATENT DOCUMENTS 4,005,134  1/1977  Markezich ..................... 260/520 E

*Primary Examiner*—Paul J. Killos
*Attorney, Agent, or Firm*—William A. Teoli; Joseph T. Cohen; Charles T. Watts

[57] ABSTRACT

A method is described for making organic polycarboxylic acids or anhydrides, such as aromatic ether bis(phthalic acid)s, based on a cyclic imide-cyclic anhydride exchange reaction at elevated temperatures in the presence of water. In addition to making organic polycarboxylic acid, organic imides are also generated.

11 Claims, No Drawings

METHOD FOR MAKING ORGANIC POLYCARBOXYLIC ACIDS

The present invention relates to a method for making organic polycarboxylic acids or anhydrides. More particularly, the present invention relates to an exchange reaction between an organic imide and an organic carboxylic acid or anhydride to make a different organic imide and an organic carboxylic acid.

Prior to the present invention, M. Michman et al, J. Chem. Soc., p. 3856, 1971, Organic Reactions in Melts and Solids, discussed various transacylation reactions involving diacylanilines with monobasic or dibasic carboxylic acids, such as phthalic acid. Meyers, U.S. Pat. No. 3,956,125, taught that tetra-acids and dianhydrides can be made by initially forming a diimide intermediate which can thereafter be hydrolyzed to the corresponding tetra-acid followed by dehydration of the tetra-acid to the corresponding dianhydride. Although Michman et al and Meyers methods can be used in particular situations to make specific carboxylic acids, they are unsuitable in many instances. Michman et al's method, for example, can not be used to make cyclic anhydrides or the corresponding polycarboxylic acids thereof. Meyers teaches that a diimide intermediate is difficult to hydrolyze if it is N-alkyl substituted instead of N-aryl substituted. The N-alkyl substituted diimide intermediate of Meyers can be converted to the dihydrazide which is thereafter oxidized and hydrolyzed to the tetra-acid. If the oxidation is conducted in the presence of an alkali metal hydroxide, the resulting tetra-acid salt must be neutralized to produce the tetra-acid.

The present invention is based on the discovery that polycarboxylic acids and anhydrides of the formula,

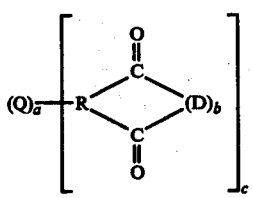

can be made by an imide-anhydride exchange reaction, where Q is monovalent or divalent, R is a $C_{(1-30)}$ polyvalent organic radical, D is selected from —O— and —OH, "a" is 0 or 1, "b" and "c" are respectively 1 or 2, and when "a" is 1 and "c" is 1, Q is selected from $R^1$, $R^1O—$, and $R^1S—$ and when "a" is 1 "c" is 2, Q is selected from —O—, —S—, —$R^2$—, —$OR^2O$—, —$SR^2S$— and —$OR^2XR^2O$—, where $R^1$ and $R^2$ are defined below and X can be

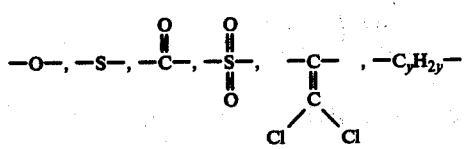

and y is equal to 0 to 5 inclusive.
The above imide-anhydride exchange can be shown as follows:

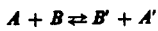

where A and A' are imides and B and B' are anhydrides. A mixture of a first imide of the formula,

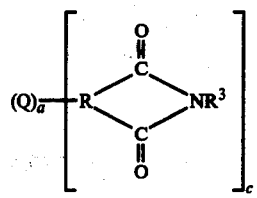

and a first dicarbonyl compound of the formula,

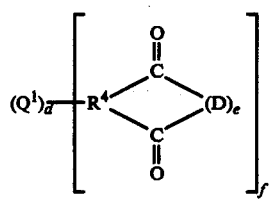

is heated in the presence of water at a temperature of at least 100° C., to produce the polycarboxylic acid of formula (1) and a second imide of the formula,

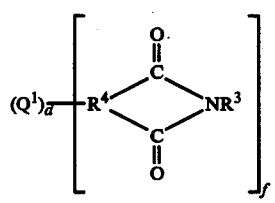

where R and $R^4$ can be the same or different polyvalent organic radicals as defined more particularly below, $R^3$ is H or $C_{(1-20)}$ monovalent organic radical and Q and $Q^1$ can be the same or different monovalent or divalent radicals as defined more particularly below and "d", "e" and "f" have the same values respectively as "a", "b" and "c".

In addition to radicals defined above, Q and $Q^1$ of formulas 1 and 3 are the same or different radicals, such as where $R^1$ is $C_{(6-13)}$ aryl radicals, for example, phenyl, tolyl, xylyl, etc; $C_{(1-8)}$ alkyl, for example, methyl, ethyl, propyl, etc; $R^2$ is selected from arylene radical, such as phenylene, xylylene, tolylene, etc., and $C_{(1-8)}$ alkylene, for example, methylene, dimethylene, trimethylene, etc.; $R^1$ and $R^2$ as previously defined also include halogenated derivatives, such as chlorophenyl, bromotolyl, chlorophenylene, chloromethyl, bromo butyl, etc. Q and $Q^1$ are preferably selected from

such as

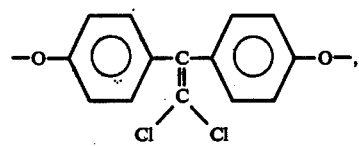

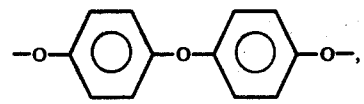

-continued

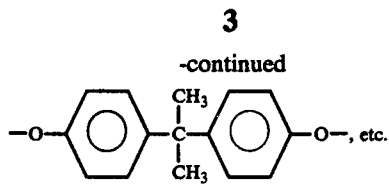

Radicals included by R and R⁴, are for example, divalent radicals, such as

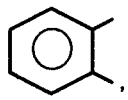 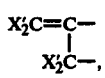

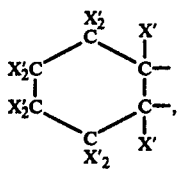 

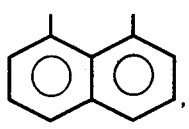 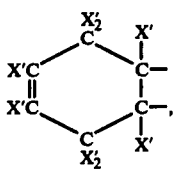

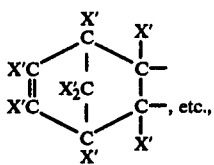

where X' can be hydrogen, chloro, or methyl.
In addition, R and R⁴ can be trivalent radicals, such as

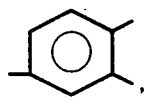

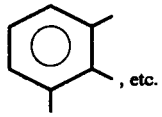

Radicals included by $R^3$, are for example, H or $C_{(1-8)}$ alkyl, such as methyl, ethyl, propyl, butyl, etc.; $C_{(6-13)}$ aryl, e.g., phenyl, etc., and halogenated derivatives thereof, such as chlorophenyl, bromo-tolyl, etc.

In a preferred procedure, there is provided a method for making aromatic ether phthalic acid of the formula,

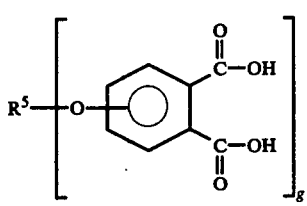

(5)

where $R^5$ is a $C_{(6-30)}$ aromatic radical and "g" is an integer equal to 1 or 2, and $R^5$ is monovalent when "g" is 1, and $R^5$ is divalent when "g" is 2, which comprises (1) heating at a temperature of at least 100° C., a mixture comprising water, phthalic anhydride or phthalic acid and aromatic ether N-organo phthalimide of the formula,

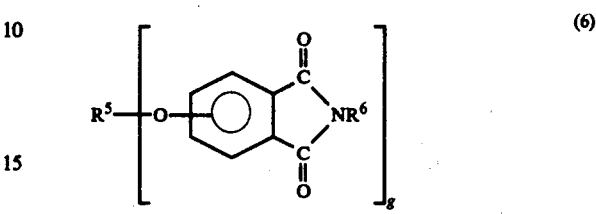

(6)

to produce a mixture comprising the aromatic ether phthalic acid and an N-organo phthalimide of the formula,

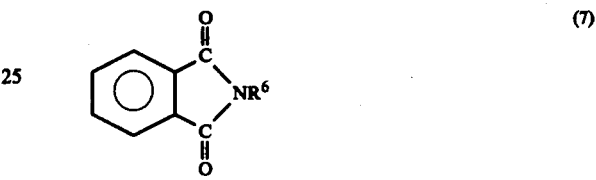

(7)

(2) effecting the separation of the N-organo phthalimide from the mixture of (1), and (3) recovering the aromatic ether phthalic acid, where $R^6$ is H or $C_{(1-20)}$ monovalent organo radical and selected from $R^3$ radicals as previously defined.

Radicals included by $R^5$ are, for example,

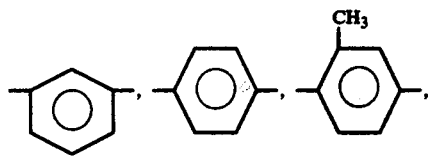

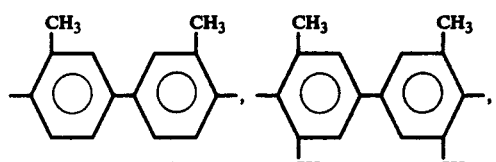

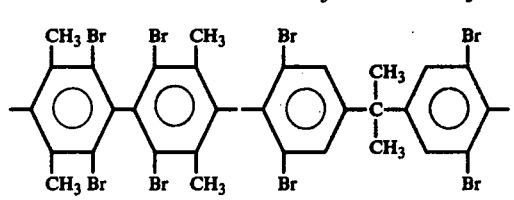

and divalent organic radicals of the general formula,

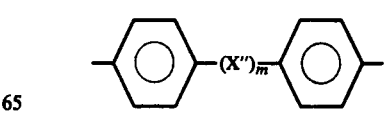

where X" is a member selected from the class consisting of divalent radicals of the formulas, $-C_yH_{2y}-$,

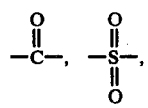

—O—, and —S—, where m is 0 or 1, y' is a whole number from 1 to 5.

In a further aspect of the invention, there is provided a method for making aromatic ether phthalic acid of the formula,

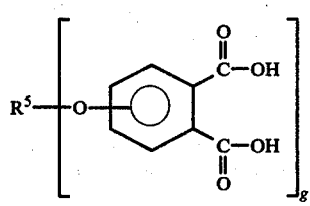

(8)

where $R^5$ and "g" are as previously defined, which required prior to the present invention, the hydrolysis in the presence of base of an aromatic ether N-alkylphthalimide of the formula,

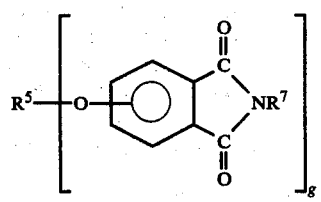

(9)

and $R^7$ is a $C_{(1-8)}$ alkyl radical, resulting in the production of an aromatic ether phthalic acid salt and involving the steps of, (A) converting the aromatic ether N-alkyl phthalimide to the corresponding hydrazide, (B) the oxidation of the hydrazide in the presence of base, and (C) the neutralization of the resulting aromatic ether phthalic acid salt, the improvement which comprises, (1) heating the aromatic ether N-alkyl phthalimide in the presence of water and phthalic anhydride or phthalic acid under sealed conditions to effect the direct exchange between the phthalic anhydride or phthalic acid and the aromatic ether N-alkyl phthalimide to produce a mixture comprising the aromatic ether phthalic acid and N-alkyl phthalimide, and (2) effecting the separation of the N-alkyl phthalimide from the mixture of (1), thereby eliminating steps of forming the aromatic ether phthalazide, the oxidation of the hydrazide in the presence of base and the neutralization of the resulting aryloxy ether phthalic acid salt.

Included by the polycarboxylic acids and anhydrides of formula (1) which can be made by practicing the method of the present invention are, for example,

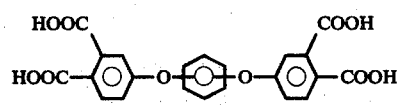

-continued

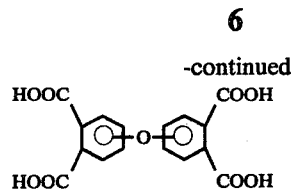

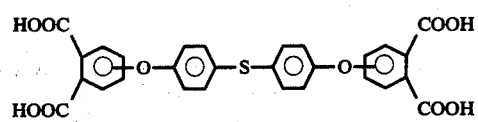

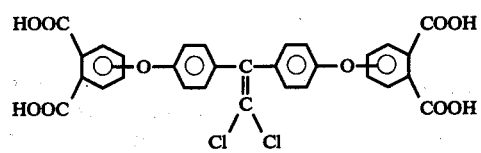

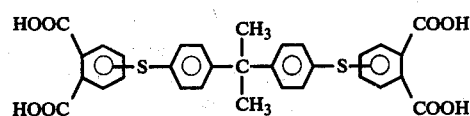

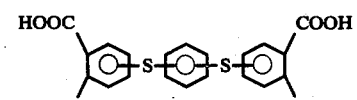

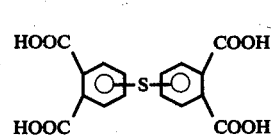

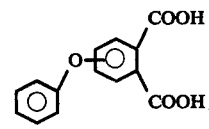

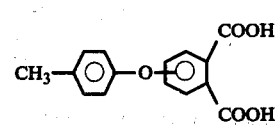

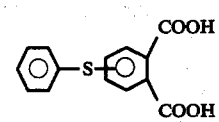

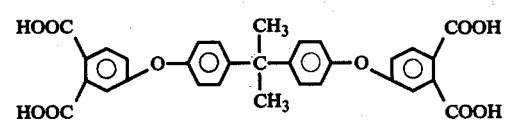

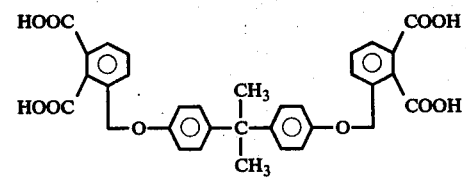

Some of the preferred imides included by formula (2) and methods for making them are shown by Heath et al U.S. Pat. No. 3,879,428, assigned to the same assignee as the present invention. For example, a phthalimide of the formula,

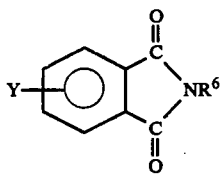

(10)

where $R^6$ is as previously defined and Y is a displaceable group selected from nitro, fluoro, chloro, etc., reacted with an alkali diphenoxide of the formula

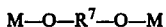

(11)

where M is a metal ion of an alkali metal selected from sodium, potassium, etc., and $R^7$ is selected from —$R^2$X-$R^2$— radicals as previously defined. A bisimide is formed by a displacement reaction which can be used in accordance with the practice of the method of the invention to provide polycarboxylic acids or anhydrides thereof as well as novel N-organo substituted phthalimides as shown by the following equation

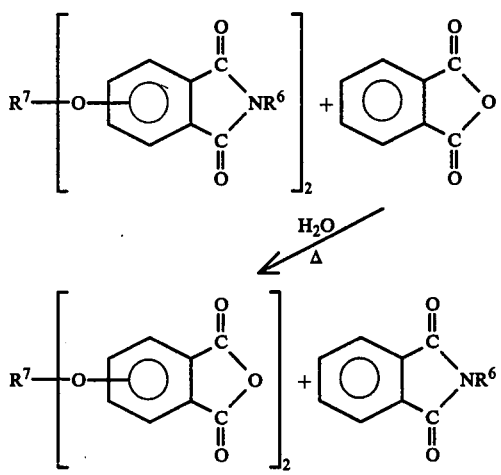

Among the alkali diphenoxides of formula (11) are alkali metal salts of the following dihydric phenols:
2,2-bis(2-hydroxyphenyl)propane;
2,4'-dihydroxydiphenylmethane;
bis-(2-hydroxyphenyl)methane;
2,2-bis-(4-hydroxyphenyl)propane;
1,1-bis-(4-hydroxyphenyl)ethane;
1,1-bis-(4-hydroxyphenyl)propane;
2,2-bis-(4-hydroxyphenyl)-pentane;
3,3-bis-(4-hydroxyphenyl)pentane;
4,4'-dihydroxybiphenyl;
4,4'-dihydroxy-3,3',5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfide;
hydroquinone;
resorcinol;
3,4'-dihydroxydiphenylmethane;
4,4'-dihydroxybenzophenone; and
4,4'-dihydroxydiphenylether.

The method of the present invention also includes a method for making aryloxy anhydrides, based on the following equation:

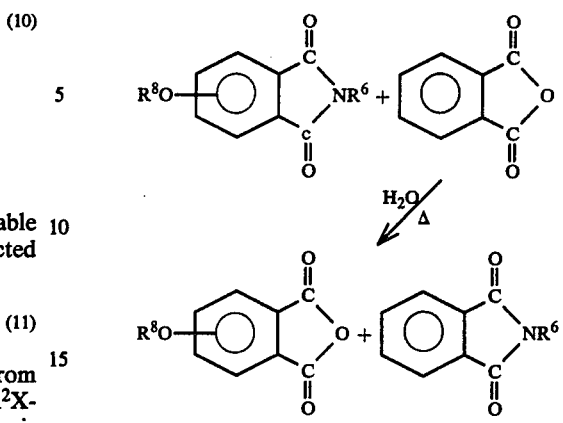

where $R^6$ is as previously defined and $R^8$ is selected from $C_{(6-13)}$ aromatic organic radicals, such as phenyl, tolyl, xylyl, chlorophenyl, etc.

As previously indicated, the above described exchange reaction between the imide of formula (2), referred to hereinafter as the "bisimide" and the dicarbonyl compound of formula (3), referred to hereinafter as "phthalic anhydride", requires the presence of water in the production of the polycarboxylic acid of formula (1), or "tetra-acid" and the imide of formula (4) or "phthalimide". In addition to water, there also can be employed as catalysts, acids such as sulfuric, phosphoric, hydrochloric, methanesulfonic, fluoroboric, toluenesulfonic, acetic, butyric, trifluoroacetic acids, etc.; metal salts, such as $FeCl_3$, $ZnCl_2$, $SnCl_4$, $AlCl_3$ and their bromides, etc.

In the practice of the invention, a mixture of the bisimide and phthalic anhydride is heated in the presence of water or an aqueous catalyst mixture. Preferably, the heating is effected in a closed system, such as an autoclave or reactor to maintain the presence of water. The mixture is heated at a temperature of at least 100° C. with agitation and thereafter the mixture is allowed to cool to ambient temperatures. The mixture can then be stripped of volatiles, or bisimide exchange product, such as imide diacid, or tetra-acid, can be recovered by standard techniques. In the event that the reaction mixture is stripped of volatiles at temperatures of up to 200° C. under reduced pressure, the resulting residue of the reaction mixture consisting essentially of bisimide exchange product can be mixed further with an additional phthalic anhydride and water and heated in a closed system, as previously described, to effect the further conversion of the bisimide to the tetra-acid. Depending upon the ratio of phthalic anhydride to bismide initially used and the number of reaction cycles employed, it has been found that complete conversion of the bisimide to the tetra-acid can be effected.

It has been found that a proportion of from 1 mol of phthalic anhydride to up to 20 mols of phthalic anhydride per mol of bisimide will provide for effective results. Temperatures in the range of from 100° C. to 300° C., and preferably from 150° C. to 250° C.

The proportion of water can vary from about 0.01 part to 100 parts of water per part of bisimide and preferably from 0.1 part to 10 parts. Metal halide catalysts can be used at from 0.01% to 10%, based on the weight of the bisimide.

The reaction can be conducted in an autoclave, ampoule, or other closed reaction vessel to maintain the presence of water while the mixture is agitated. In certain situations, the reaction can be conducted at atmospheric pressure by bubbling steam into the melt of the mixture. In addition to the tetra-acid, for example the reaction mixture can contain imide-diacids of the formula

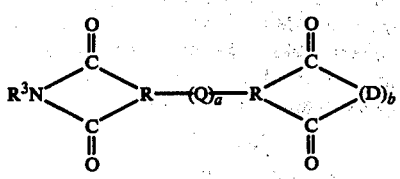

where R, $R^3$, Q, D and a are as previously defined. Some of the imide diacids provided by the method of the pesent invention are as follows:

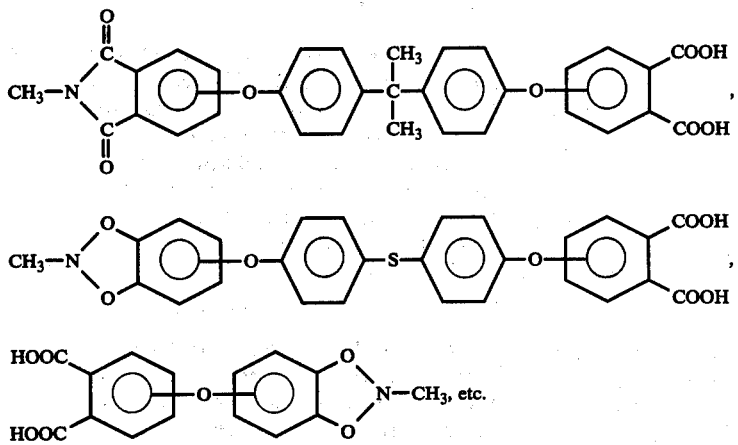

Recovery of the tetra-acid from the mixture can be achieved initially by effecting removal of the phthalimide which can be achieved by solvent extraction, distillation, liquid chromotography, etc. Other techniques which can be used are direct extraction of the tetra-acid using an aqueous alkali carbonates or bicarbonates, such as the corresponding sodium or potassium salts, etc.

The tetra-acids and anhydrides made in accordance with the method of the present invention can be employed to make polyetherimides, as shown by Heath et al, U.S. Pat. No. 3,875,116. In addition, the derivatives of diacids made by the present invention can be utilized as plasticizers for various organic resins, such as polyvinyl chloride, etc., where there can be utilized from 1 to 50 parts of the anhydride, per 100 parts of organic resin.

In order that those skilled in the art will be better able to practice the invention, the following examples are given by way of illustration and not by way of limitation. All parts are by weight.

EXAMPLE 1

A mixture of 25.3 parts of 4-phenoxy-N-methylphthalimide, 29.6 parts of phthalic anhydride and 50 parts of water was heated in an autoclave for 2 hours at 200° C. The mixture was then allowed to cool to ambient conditions. The resulting mixture was then heated to a temperature of 170° C. under atmospheric conditions. The residue of the mixture was then distilled under reduced pressure. There was obtained 18.7 parts of a first fraction boiling at 182° C. at 55 torr. There was also obtained 9.7 parts of a second fraction boiling at 182° C. at 50 torr.

The above fractions were combined and heated with about 25 parts of water at reflux for 20 minutes. The mixture was then allowed to cool to room temperature and filtered. The solid was then dispersed in about 25 parts of methylene chlordie and stirred at reflux for 10 minutes. The mixture was then allowed to cool to room temperature. Upon cooling, a precipitate resulted which was filtered. The methylene chloride mother liquor was evaporated to dryness, resulting in the production of 7.39 parts of product. Based on its infrared spectrum, the product was N-methylphthalimide. The crystalline precipitate recovered from the original methylene chloride solution was then washed with additional methylene chloride. There was obtained 18.3 parts of pure phthalic acid.

In addition to the above described two fractions recovered from the original autoclave reaction mixture resulting in the production of phthalic acid and N-methylphthalimide, there was also obtained 13.4 parts of a fraction at 257°-258° C. at 32 torr. In addition to the aforementioned fraction, there was also obtained 10.5 parts of a distillation residue. The aforementioned fraction of 13.4 parts was refluxed with about 20 parts of water for 20 minutes. The mixture was allowed to cool and combined with about 25 parts of methylene chloride with stirring. The resulting mixture was filtered, resulting in 9.6 parts of filtration product. Based on its infrared spectrum, the filtration product was found to be 4-phenoxyphthalic acid. The methylene chloride mother liquor was evaporated to dryness, resulting in 4 parts of residue. Its infrared spectrum showed it was pure 4-phenoxy-N-methylphthalimide.

The 10.5 parts distillation residue of the original autoclave mixture was found to be a mixture of 61% by weight of 4-phenoxyphthalic anhydride and 39% by weight of 4-phenoxy-N-methylphthalimide.

The above results show that an exchange occurred between 4-phenoxy-N-methylphthalmide and phthalic anhydride, resulting in a 46% yield of N-methylphthalimide and a 64% yield of 4-phenoxyphthalic anhydride or acid. This conversion of 4-phenoxy-N-methylphthalimide to 4-phenoxyphthalic anhydride was achieved in a direct manner without any requirement for converting the 4-phenoxy-N-methylphthalimide to the corresponding hydrazide or the base hydrolysis thereof, resulting in the prdouction of metal salt requiring the neutralization and heating of the resulting phthalic acid.

EXAMPLE 2

A mixture of 2.32 parts of maleic acid, 2.23 parts of N-phenyl phthalimide and 20 parts of water is heated under sealed conditions for 2 hours at 180° C. The reaction mixture is then allowed to cool to ambient conditions and distilled under vacuum. Maleic anhydride is initially recovered followed by phthalic anhydride and N-phtnyl maleimide. There is obtained a yield of 16% by weight of phthalic anhydride and 14.1% by weight of N-phenylmaleimide.

EXAMPLE 3

A mixture of 20.71 parts of 2,2-bis[4-(N-methylphthalimide-4-oxy)phenyl]propane, 125.32 parts of phthalic anhydride and 1.35 part of p-toluene sulfonic acid monohydrate was heated at 180° C. for 20 hours under sealed conditions. The mixture was then allowed to cool to atmospheric conditions. It was then distilled at a temperature of 250° and a pressure of 60 mm Hg, resulting in the production of a distillate in the form of a mixture of phthalic anhydride and N-methylphthalimide. The residue was then analyzed by high pressure liquid chromatography (HPLC). There was obtained 7% by weight of 2,2-bis[4-(3',4'-dicarboxyphenoxy)-phenyl]propane dianhydride, 40% by weight of 2-[4-(3,4-dicarboxyphenyl)phenyl]-2-[4-(N-methylphthalimide-4-oxy)phenyl]propane anhydride and 53% by weight of 2,2-bis[4-(N-methylphthalimide-4-oxy)-phenyl]propane.

The above liquid residue was then separated into its component parts by HPLC. The dianhydride was found to have a melting point of 183°–187° C. and the imide anhydride was found to have a melting point of 111°–116° C. The identity of the imide anhydride having the following formula,

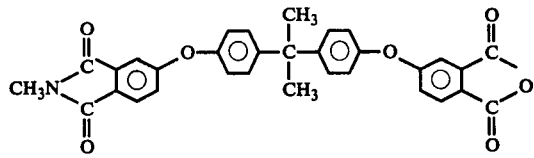

was confirmed by its infrared spectra: anhydride carbonyls — 1850, 1775 cm$^{-1}$; imide carbonyl — 1706 cm$^{-1}$, Calculated for $C_{32}H_{23}NO_7$ by mass spectroscopy: 533.146. Found: 533.148. Those skilled in the art would know that this imide anhydride would be useful as a plasticizer for organic polymers.

EXAMPLE 4

In accordance with the procedure of Example 3, a mixture of 136 parts of the bisimide, 148 parts of phthalic anhydride and 2.7 parts of water was heated for 20 hours at 200° C. The mixture was then allowed to cool to atmospheric conditions and distilled at 220° C. at 60 mm Hg pressure for 15 minutes. The distillate consisted principally of phthalic anhydride and N-methylphthalimide. The residue was then analyzed by high pressure liquid chromotography. There was obtained 6% by weight of the imide anhydride of Example 3, based on the weight of the bisimide employed in the original mixture.

The above procedure was repeated, except that in addition to the above-mentioned ingredients, 8.2 parts of trichloroacetic acid was used in the mixture. In addition to trichloroacetic acid, a further mixture was made following the same procedure, except that in the place of the 8.2 parts of the trichloroacetic acid and 2.7 parts of water, there was utilized 8.6 parts of para-toluene sulfonic acid and 0.8 part of water. Other mixtures were also heated with added catalyst, except that the water content was significantly increased. The following results were obtained, where BPA-DA is 2,2-bis[4-(3,4-dicarboxyphenoxy)phenyl]propane dianhydride and BPAIA is the corresponding imide anhydride.

TABLE I

| Catalyst | Catalyst (parts) | Parts H$_2$O | Time (hrs) | Wt % BPA-DA | Wt % BPA-IA |
|---|---|---|---|---|---|
| None | — | 2.7 | 20 | 0 | 6 |
| CCl$_3$COOH | 8.2 | 2.7 | 20 | 3 | 24 |
| pTSOH$^a$ | 8.6 | 0.9 | 20 | 28 | 49 |
| None | — | 30.6 | 1 | 2 | 24 |
| None | — | 90.0 | 1 | 18 | 50 |

$^a$p-toluene sulfonic acid

The above results show the effect water and catalyst have on the yield of the BPA-DA and BPA-IA. Unlike Example 3, where water was introduced into the reaction as a mono hydrate of p-toluene sulfonic acid, water was employed directly. Table I also shows that water can be used free of catalyst, but that a significantly higher amount of water is required in the absence of catalyst to obtain a satisfactory yield of the BPA-DA or the BPA-IA.

EXAMPLE 5

The procedure of Example 1 was repeated, except that various catalysts were employed with and without water to determine the effect of such catalyzed mixture on the yield of the 4-phenoxyphthalic anhydride. A mixture of 29 parts of N-methyl-4-(p-methylphenoxy)phthalimide, and 25 parts of phthalic anhydride were heated under sealed conditions in the presence of 3.6 parts of water which was used either alone or in the presence of another catalyst.

The following results are shown in Table II, where weight percent of aryloxy anhydride is 4-phenoxyphthalic anhydride, based on the weight of the aryloxy-substituted phthalimide used in the mixture.

TABLE II

| Catalyst | Parts Catalyst | Time/Temp (hrs) (C°) | Wt % Aryloxy Anhydride |
|---|---|---|---|
| pTSOH | 3.4 | 20/180° | 44 |
| FeCl$_3$ | 3.2 | 20/180° | 39 |
| — | — | 21/180° | 2 |
| — | — | 21/250° | 13 |
| MeSO$_3$H$^b$ | 1.9 | 20/180° | 53 |

$^b$methane sulfonic acid

The above results show that when small amounts of water are used in the absence of a catalyst, the yields of aryloxy anhydride is significantly reduced. Another mixture was heated in the absence of water containing 3.2 parts of ferric chloride, resulting in a 4 weight percent of aryloxy anhydride after heating at 180° C. for 20 hours.

EXAMPLE 6

A mixture of 54.6 parts of 2,2-bis[4-(N-methyl phthalimide-4-oxy)phenyl]propane, 148 parts of phthalic anhydride and 200 parts of water is heated with stirring in an autoclave at 210° C. for 3 hours and then cooled to room temperature. The resulting mixture is distilled under a reduced pressure of approximately 50 Torr. After the initial removal of the water, a mixture of phthalic anhydride and N-methyl phthalimide is collected at 180° C.-185° C.-50 Torr, leaving approximately 52 parts of a residue. The residue consists of the starting bisimide, the corresponding monoimide-anhydride and the resulting dianhydride in a ratio of by weight of approximately 5% bisimide, 32% monoimide-anhydride and 63% dianhydride.

The above procedure is repeated, except that a mixture of 52 parts of the residue, 128 parts of phthalic anhydride and 200 parts of water are employed in the mixture. The reaction mixture is again distilled at 185° C.-50 Torr to remove volatile fractions. There is obtained 50 parts of residue. It is found to consist of 91 percent by weight of 2,2-bis[4-(3,4-dicarboxyphenoxy)-phenyl]propane dianhydride. The crude product is recrystalized from 400 parts of toluene and a yield of 39 parts of the dianhydride is obtained having a melting point of 185° C.-187° C.

Although the above examples are limited to only a few of the very many variables, such as reactants, catalysts, conditions, etc., which can be used in the practice of the method of the present invention, it should be understood that the method of the present invention is directed to the production of the polycarboxylic acids and anhydrides of formula (1), based on an interchange between imides of formula (2) and dicarbonyl compounds of formula (3). As shown by copending application RD-9112 of Jimmy L. Webb, filed concurrently herewith and assigned to the same assignee as the present invention, recovery of the imide of formula (4) can be effected by venting the reaction mixture under equilibrium conditions.

What we claim as new and desire to secure by Letters Patents of the United States is:

1. A method which comprises,
   (1) heating at a temperature of at least 100° C. in the presence of water, a mixture comprising a first organic imide of the formula,

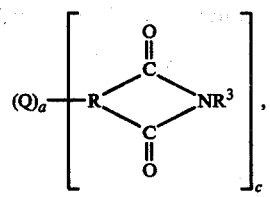

and a first organic anhydride, or polycarboxylic acid precursor thereof of the formula,

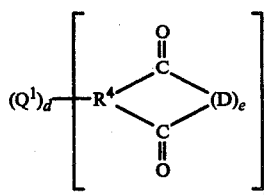

for a time sufficient to effect an imide-anhydirde exchange to produce a mixture comprising a second organic imide of the formula,

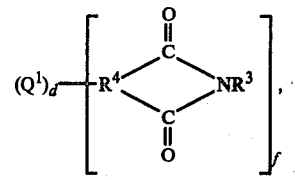

and a second polycarboxylic acid or anhydride thereof of the formula,

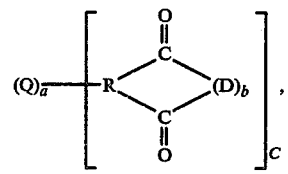

(2) effecting the separation of the second organic imide or second polycarboxylic acid or anhydride from the mixture of (1), where Q and $Q^1$ are the same or different monovalent radicals selected from $R^1$—, $R^1O$—, $R^1S$—, the same or different divalent radicals selected from —O—, —S—, —$R^2$—, —O—$R^2$—O—, —S—$R^2$—S— and —O$R^2$X-$R^2O$—, and Q and $Q^1$ can have different valences, X is selected from

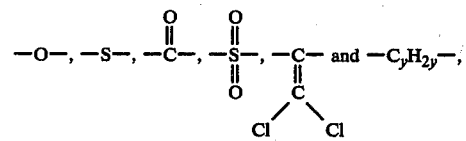

and y is equal to 0 to 5 inclusive, R and $R^4$ are selected from the same or different polyvalent organic radicals, $R^1$ is selected from $C_{(6-13)}$ monovalent aromatic radicals, and $C_{(1-8)}$ alkyl radicals, $R_2$ is selected from $C_{(6-13)}$ divalent aromatic organic radicals and $C_{(1-8)}$ alkylene radicals, $R^3$ is selected from H and $C_{(1-20)}$ monovalent organic radicals, D is selected from —O— and —OH, "a" is a whole number equal to 0 or 1, "b" is an integer equal to 1 or 2 and "c" is an integer equal to 1 or 2, when "a" and "c" are respectively 1, Q is a monovalent radical, and when "a" is 1 and "c" is 2, Q is a divalent radical, and "a", "b" and "c" and "d", "e" and "f" have the same values respectively.

2. A method in accordance with claim 1, for making an organic imide.

3. A method in accordance with claim 1, where the first organic imide is an organic bisimide.

4. A method in accordance with claim 1, where the imide anhydride exchange results in the production of an imide dicarboxylic acid.

5. A method which comprises
   (1) heating at a temperature of at least 100° C. in the presence of water, a mixture comprising a bisimide of the formula,

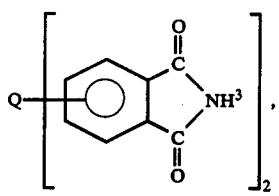

and phthalic anhydride or phthalic acid to produce a mixture comprising

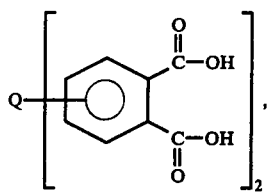

and an N-organo phthalimide of the formula,

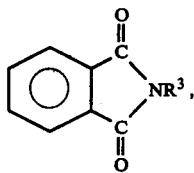

(2) effecting the separation of the N-organo phthalimide from the mixture of (1), where Q is a divalent radical selected from —O—, —S—, —R$^2$—, —O—R$^2$—O—, —S—R$^2$—S— and —OR$^2$XR$^2$O—, X is selected from —O—, —S—,

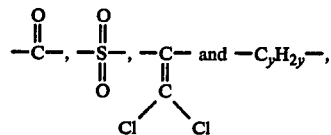

and y is equal to 0 to 5 inclusive, R$^2$ is selected from C$_{(6-13)}$ divalent aromatic organic radicals and C$_{(1-8)}$ alkylene radicals, and R$^3$ is selected from H and C$_{(1-20)}$ monovalent organic radicals.

6. A method in accordance with claim 5, where separation of the resulting N-organophthalimide is achieved by distillation.

7. A method in accordance with claim 5, where Q is

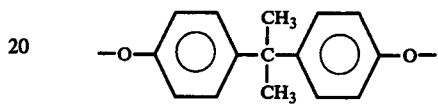

and R$^3$ is methyl.

8. A method in accordance with claim 5, where the mixture is heated in the presence of a ferric chloride catalyst.

9. A method in accordance with claim 5, where the mixture is heated under sealed conditions.

10. A method in accordance with claim 5, where the mixture is distilled after the mixture has been restored to ambient conditions to effect the separation of N-organo phthalimide from a reaction mixture comprising anhydride and

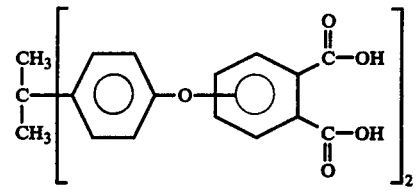

11. A method in accordance with claim 5, where the separation of the N-alkyl phthalimide is achieved by solvent extraction.

* * * * *